(12) United States Patent
Buyse et al.

(10) Patent No.: US 9,992,994 B2
(45) Date of Patent: Jun. 12, 2018

(54) AGRICULTURAL AND DETERGENT COMPOSITIONS CONTAINING A TERTIARY AMIDE AS ADJUVANT OR AS SURFACTANT

(75) Inventors: Kurt Buyse, Sint-Andries (BE); Kristof Moonen, Hamme (BE)

(73) Assignee: Taminco BVBA, Ghent (BE)

( * ) Notice: Subject to any disclaimer, the term of this patent is extended or adjusted under 35 U.S.C. 154(b) by 335 days.

(21) Appl. No.: 14/115,059

(22) PCT Filed: May 4, 2012

(86) PCT No.: PCT/EP2012/058270
§ 371 (c)(1),
(2), (4) Date: Dec. 2, 2013

(87) PCT Pub. No.: WO2012/150343
PCT Pub. Date: Nov. 8, 2012

(65) Prior Publication Data
US 2014/0080708 A1    Mar. 20, 2014

(30) Foreign Application Priority Data
May 4, 2011    (EP) .................... 11164846

(51) Int. Cl.
| | | |
|---|---|---|
| *A01N 25/30* | (2006.01) | |
| *C11D 3/32* | (2006.01) | |
| *C11D 7/32* | (2006.01) | |
| *C07C 233/36* | (2006.01) | |
| *C11D 1/62* | (2006.01) | |

(52) U.S. Cl.
CPC ............ *A01N 25/30* (2013.01); *C07C 233/36* (2013.01); *C11D 1/62* (2013.01); *C11D 3/32* (2013.01); *C11D 7/3263* (2013.01)

(58) Field of Classification Search
CPC ........... C07C 233/36; C11D 1/62; C11D 3/32; C11D 7/3263; A01N 25/30
USPC ...................................................... 504/206
See application file for complete search history.

(56) References Cited

U.S. PATENT DOCUMENTS

| | | |
|---|---|---|
| 3,234,153 A | 2/1966 | Britain |
| 4,049,591 A | 9/1977 | McEntire et al. |
| 5,869,653 A | 2/1999 | Johnson |
| 5,958,439 A | 9/1999 | Gubelmann |
| 6,172,262 B1 | 1/2001 | McQuade et al. |
| 6,458,860 B1 | 10/2002 | Humbert et al. |
| 6,747,164 B2 | 6/2004 | Gustaysson et al. |
| 7,332,467 B2 | 2/2008 | Schneiderman et al. |
| 7,678,755 B2 | 3/2010 | Scheibel et al. |

FOREIGN PATENT DOCUMENTS

| | | | |
|---|---|---|---|
| EP | 0 257 686 A1 | 3/1988 | |
| EP | 0 638 236 A1 | 2/1995 | |
| EP | 0 911 384 A2 | 4/1999 | |
| EP | 0911384 | * 4/1999 | .......... C10M 173/02 |
| FR | 2 737 390 A1 | 2/1997 | |
| PL | 388525 A1 | 7/2009 | |
| WO | WO 97/05779 A1 | 2/1997 | |
| WO | WO 98/47860 A1 | 10/1998 | |
| WO | 01/95720 A1 | 12/2001 | |
| WO | WO 01/95720 A1 | 12/2001 | |
| WO | WO 2006/034426 A1 | 3/2006 | |
| WO | 2008/068214 A2 | 6/2008 | |
| WO | 2008/069826 A1 | 6/2008 | |
| WO | WO 2008/106466 A1 | 9/2008 | |
| WO | 2010/036996 A2 | 4/2010 | |
| WO | 2011/026800 A2 | 3/2011 | |

OTHER PUBLICATIONS

Renata Skrzela et al.: "Experimental and Theoretical Approach to Nonequivalent Adsorption of Novel Dicephalic Ammonium Surfactants at the Air/Solution Interface"Journal of Physical Chemistry,Jul. 28, 2010, vol. 114, pp. 10471-10480.
International Search Report and Written Opinion with dated Aug. 2, 2012 in International Application No. PCT/EP2012/058270.
Hall, H.K., Jr.; "Correlation of the Base Strengths of Amines"; J. Am. Chem. Soc.; Oct. 20, 1957; vol. 79 (20); pp. 5441-5444.
Khalil, et al.; "New Insights into M(II)—Hydroxamate Interactions: The Electro-Analytical Behavior of Metal(II) Complexes Involving Monohydroxamic Acids and Diamines in an Aqueous Medium"; J. Chem. Eng. Data; 2008; 53; pp. 2318-2327.
Para et al.; "Surface activity of cationic surfactants, influence of molecular structure"; Colloids and Surfaces A: Physicochemical and Engineering Aspects; Elsevier; 365; 2010; pp. 215-221.

(Continued)

*Primary Examiner* — Johann R Richter
*Assistant Examiner* — Danielle Sullivan
(74) *Attorney, Agent, or Firm* — Robert C. Morriss (57) ABSTRACT

The invention relates to agrochemical compositions comprising new biodegradable bisaminopropylamides of formula (I)

$$R^3\text{-}N(R^2)\text{-}CH_2CH_2CH_2\text{-}N(C(=O)R^1)\text{-}CH_2CH_2CH_2\text{-}N(R^4)R^5 \quad (I)$$

or of formula (II)

$$R^6(R^3)(R^2)N^+\text{-}CH_2CH_2CH_2\text{-}N(C(=O)R^1)\text{-}CH_2CH_2CH_2\text{-}N^+(R^4)(R^5)R^6 \quad 2Y^- \quad (II)$$

and to their uses in detergent compositions. In the agrochemical compositions the bisaminopropylamides act as adjuvant for the agrochemically active compounds such as pesticides, growth regulators or fertilizers.

14 Claims, 2 Drawing Sheets

(56) References Cited

OTHER PUBLICATIONS

European Office Action dated Jun. 22, 2015 in Application No. 12 721 459.1.
Reply dated Dec. 21, 2015 in response to European Office Action dated Jun. 22, 2015 in Application No. 12 721 459.1.

* cited by examiner

AGRICULTURAL AND DETERGENT COMPOSITIONS CONTAINING A TERTIARY AMIDE AS ADJUVANT OR AS SURFACTANT

CROSS REFERENCE TO RELATED APPLICATIONS

This is a National Stage of International Application No. PCT/EP2012/058270 filed May 4, 2012, claiming priority based on European Patent Application No. 11164846.5 filed May 4, 2011, the contents of all of which are incorporated herein by reference in their entirety.

The present invention relates to agricultural compositions containing a tertiary amide as a new adjuvant and to the use of that tertiary amide as an adjuvant in agrochemical compositions and in detergent compositions containing an anionic surfactant.

A whole range of agrochemicals are applied to exert any biological effects when growing crops, for instance pesticides, plant growth regulators or plant fertilizers. Many of these compounds are applied by spraying on the leaf, and need to be taken up through the leaf's surface in order to exert their effect in the plant. Therefore, many of these agrochemicals are formulated into agricultural compositions.

By formulating agrochemicals into an agricultural composition, several effects can be obtained. The agrochemical can be made in such a form that it is easy to handle (e.g. pourable, easy to dilute for further use, . . . ), that it is stable during storage and use (for instance formation of emulsions or suspensions, efficient formation of spray droplets, . . . ), that it is more safe to use (for instance by providing dust-free products or reducing drift during spray applications) or that the active ingredient is delivered more efficiently to the target organism. The latter can be achieved for instance by improving adherence to the leafs, improving spreading and wetting on the leaf surface or enhancing penetration through the leaf's surface.

It is well known that the choice of the surfactants in the agricultural composition has a major influence on the performance of the agrochemical. Surfactants in agricultural compositions may for instance act as dispersants, wetting agents or adjuvants. However, the ability of different surfactants to enhance agrochemical effectiveness is highly unpredictable. Furthermore, the choice of a suitable surfactant is often very much dependent on the identity and physicochemical properties of the active ingredient of the composition, but also of the other constituents of the composition.

Formulators of agrochemicals tend to shift to more concentrated solutions of their active ingredients. This causes also the surfactant concentration to increase, which brings additional challenges to avoid phase separation to occur. Low temperature stability is a critical parameter to many agricultural compositions.

Due to resistance of certain weeds to certain pesticides, more and more blends of pesticides are being used. A common strategy is to use both a hydrophilic and a lipophilic pesticide in one application. This often requires the use of multiple surfactants that are effective for the individual active ingredients being present. For many active ingredients, such as for instance glyphosate, it is well known that cationic types of surfactants are very efficient. However, many cationic surfactants often are not compatible with anionic surfactants, which may be added to the composition for other purposes. Another and perhaps preferred solution would be to use one surfactant to boost the effectiveness of all active ingredients being present. Adjuvants that work well with hydrophilic pesticides, sometimes work antagonistically with lipophilic pesticides and vice versa. Therefore there is a need for adjuvants that are effective with a broad range of pesticides, from very hydrophilic to very lipophilic ones.

Another requirement nowadays is an increasing demand in most areas for compounds that are readily biodegradable. This is also the case within the agrochemical field, where adjuvants with a better biodegradability combined with a good ability to improve the uptake and efficacy of pesticides and fertilisers are being sought for.

Therefore, there is a continued need in the industry for more effective and compatible adjuvants, dispersants and surfactants, especially those utilized in delivery formulations for pesticidal components, among others. Higher efficacy results in lower application rates to achieve the same effect. Therefore, agricultural compositions with enhanced efficacy lead to lower costs, increased product safety and lower environmental impact.

A variety of surfactants has been used for this purpose, and many of them are nitrogen containing. The surfactant group that has been most widely used in this respect are the fatty amine ethoxylates, but also other types of compounds have been described as adjuvants for pesticides or fertilisers. WO2006/034426 for instance shows the use of alkoxylated alkylamine quaternary surfactants as adjuvants for glyphosate. In EP 0 257 686 the incorporation of certain alkoxylated fatty amines, amidoamines or imidazolines is shown to enhance the activity of herbicidal and fungicidal compositions.

Biodegradability of surfactants can be improved by incorporating ester or amide functionalities into the structure. EP-A1-0 638 236 describes an agricultural chemical composition containing as an adjuvant compounds of the class of esteramines. The esteramines disclosed in that publication all referred to compounds having two fatty alkyl chains. WO2008/106466 shows the use of alkanolamine esters as adjuvant/dispersant for pesticide formulations. Ester containing surfactants may, however, have the disadvantage of being prone to hydrolysis, while amide groups are much more hydrolytically stable.

EP-B1-1 289 362 describes the use of amine compounds with improved biodegradability as adjuvants for pesticides and fertilizers. The compounds are based on dialkylamino propylamine, wherein the alkyl groups are C1 to C5 fatty chains and which are converted into an amidoamine by reaction with a C8 to C22 fatty acid.

In WO 97/05779 plant protection compositions containing water-soluble active materials and one or more polyethoxylated amidoamines containing two carbon atoms between the amido and amino groups were claimed.

EP-B-1 289 362 discloses agricultural compositions comprising a pesticide, a growth regulator or a fertilizer and amidoamines, in particular diethanolaminopropylamides or dialkylaminopropylamides, as a biodegradable adjuvant. The amidoamines described in this European patent are secondary amides, i.e. they comprise a —CONN— amide group. For the preparation of these amidoamines reference is made in this prior art patent to WO 98/047860 (=EP-B-0 977 727) disclosing a process wherein a carboxylic acid is reacted with an amine to produce the corresponding amide. In the only preparation example disclosed therein, use is made of N,N-dimethylaminopropylamine (DMAPA) as primary amine which is reacted with decanoic acid to produce the corresponding secondary amide. The thus produced carboxylic amides are described in EP-B-0 977 727 as being useful as surfactants.

A drawback of the use of such primary aminopropylamines, and in particular of DMAPA, is that they have already a lot of other large-scale applications and that the production of these amines causes the formation of large amounts of byproducts, in particular of the corresponding secondary bisaminopropylamines, for which there aren't sufficient commercial applications and which therefore have to be discarded from the process as a waste material. As to the applications of DMAPA, DMAPA is for example an important intermediate for surfactants in the production of soft soaps and other products, as an intermediate for the production of betaines and fatty amine oxides. N,N-dimethylaminopropylamine is also used as a starting material in the production of flocculating agents (by its conversion to the corresponding methacrylamide monomers), road marking paints, and polyurethanes. DMAPA has also been shown to inhibit corrosion in boiler water treatment, and is an intermediate for gasoline and motor oil additives. Owing to DMAPA's wide utility, and the fact that the products it is associated with are produced at the multi-million pound per year level, there is a constant challenge to produce the N,N-dimethylaminopropylamine in high yield and selectivity, due to the high costs associated with byproduct contamination. These costs could of course also be reduced when new valuable applications of the byproducts could be found.

One of the more common methods used for the commercial production of aliphatic amines such as dimethylaminopropylamine (DMAPA) is the catalytic hydrogenation of aliphatic nitriles using either batch, suspended bed or trickle-bed hydrogenation techniques with the use of ammonia to inhibit secondary amine formation (in particular bisdimethylaminopropylamine or bisDMAPA). However, substantial amounts of ammonia are needed to be effective, and even then, several percents of secondary amines are formed. The handling of ammonia is expensive in that it requires pressurized storage, increases cycle time for loading and venting and it can present an environmental problem unless expensive recovery equipment is provided. Other processes and special hydrogenation catalysts have thus been developed to enable the production of DMAPA without added ammonia. Reference can be made for example to the process disclosed in U.S. Pat. No. 5,869,653. However, a problem remains that often a small percentage of the secondary amine coproduct is still produced for which there are in practice only small-scale applications so that relatively large amounts thereof remain as waste material.

A first possible application of the secondary amine bisDMAPA is its use in the production of a polyurethane catalyst. This application is described for example in U.S. Pat. No. 3,234,153; U.S. Pat. No. 4,049,591 and U.S. Pat. No. 6,458,860. U.S. Pat. No. 3,234,153 discloses more particularly the use of N,N-bis(dimethylaminopropyl)acetamide, and U.S. Pat. No. 6,458,860 the use of N,N-bis (dimethylaminopropyl)formamide, as a polyurethane catalyst. However, for these applications only limited amounts of bisDMAPA are needed.

As disclosed in US 2005/0202990, more particularly in Examples XXII-XXV thereof, bisDMAPA can also be used as such in effervescent tablets which are used in particular to pre-treat new garment before it is washed for the first time to lock in colours and prevent dye bleeding. BisDMAPA can moreover also be used as amine capping unit in the production of complex polyol compounds for use in cleaning compositions. Such applications are disclosed in U.S. Pat. No. 7,332,467 and U.S. Pat. No. 7,678,755.

All of these applications are not sufficient in practice to find a market for the relatively large amounts of the secondary amine byproducts produced in the production of the commercially valuable primary amine, and they are certainly not sufficient to be able to reduce the efforts made in the production of the primary amines to inhibit the formation of the secondary amines so that more secondary amine byproducts would be formed.

An object of the present invention is to find new, preferably larger scale, commercial applications for these secondary amine byproducts.

A further object of the present invention to provide an adjuvant with a broad compatibility for both charged, hydrophilic and lipophilic active ingredients and that effectively enhances their performance.

Another object of the present invention to provide an adjuvant in agrochemical compositions, or a surfactant or solubilizer in detergent composition, that shows good compatibility with anionic surfactants and is compatible with aqueous and organic media, and even more acts as a compatibilizer in high load formulations.

Still another object of the present invention to provide an adjuvant/surfactant with good biodegradability.

The present invention provides a new agrochemical composition containing at least one active ingredient selected from the group consisting of pesticides, growth regulators and/or fertilizers (in particular foliar fertilizers), and further a tertiary amide of formula (I)

or of formula (II)

wherein:
R1 is an aliphatic group having 5-23 carbon atoms, and is preferably a fatty chain;
R2, R3, R4 and R5 are independently hydrogen, —$CH_2CH_2OH$, —$CH_2CH(CH_3)OH$ or an aliphatic group with 1-5 carbon atoms, preferably 1-3 carbon atoms:

R6 is hydrogen or an aliphatic or aromatic group having 1-22 carbon atoms; and

Y⁻ is an anion.

It also provides a new detergent composition that contains at least one tertiary amide of formula (I) or formula (II) and additionally at least one anionic surfactant, the detergent composition being preferably a water-based liquid composition. The detergent composition preferably comprises at least one soap.

By the expression "an aliphatic group having x-y carbon atoms" or "an aliphatic group with x-y carbon atoms" is meant in the present specification a linear or branched Cx to Cy carbon chain (Cx and Cy included) which may be saturated or not.

Similar to DMAPA amides, amides can be formed out of bisDMAPA. Opposite to DMAPA amides, which are secondary amides, the amides resulting from acylation of bisDMAPA are tertiary amides. It has been found quite by surprise that these new tertiary amides have properties that are significantly different from the secondary DMAPA amides, but that they can nevertheless still be used in the same or similar applications and moreover also in other applications, in particular as adjuvant for biologically active compounds such as pesticides, growth regulators and fertilizers and as solubilizer or surfactant in detergent compositions. An important advantage of these tertiary amides is that they can be made starting from the secondary amine byproducts, such as bisDMAPA, instead of from the primary amines such as DMAPA. A further important advantage of these tertiary amides is that they are also biodegradable, as has been shown in example 3.

In a preferred embodiment the R2 and R3 groups of the tertiary amide are the same as the R4 and R5 groups, i.e. the amide is a symmetric amide.

In a further preferred embodiment the tertiary amide is free of the corresponding secondary amides of formula (III) and (IV):

(wherein the different R groups have the same meaning as in formula's (I) and (II)) or comprises per 100 moles of said tertiary amide at the most 50 moles, preferably at the most 25 moles, of these corresponding secondary amides of formula (III) and (IV).

R1 is preferably an aliphatic group, in particular a fatty chain, having 5-13 carbon atoms (i.e. a C5 to C13 carbon chain), preferably 5-9 carbon atoms. This embodiment is especially advantageous when the amide is a diamine of formula (I). It has indeed been found rather surprisingly that notwithstanding the absence of ionic groups, such tertiary amides are completely soluble in water and also in apolar solvents such as dodecane. This is not only the case when one or more of the R2, R3, R4 and R5 groups are ethanol and/or tertiary propanol groups, but also when these groups are alkyl groups, in particular C1 to C3 alkyl groups. The R2, R3, R4 and R5 groups are preferably methyl groups. The corresponding DMAPA amides, on the other hand, show only poor water solubility.

R1 may also be a longer chain aliphatic group, in particular an aliphatic group having 7-21 carbon atoms, preferably 9-17 carbon atoms. This embodiment is especially advantageous when the amide is a diammonium salt of formula (II). It has been found that such a diammonium salt can also act as a solubilizer (in particular in water) but especially as a surfactant. As a surfactant it is compatible with anionic surfactants, especially when R6 is hydrogen or an aliphatic group having 1 to 3 carbon atoms, with R6 being preferably a methyl group. In a preferred embodiment, R1 is an aliphatic group having 9 to 15 carbon atoms, preferably 9 to 13 carbon atoms, in order to achieve optimal foam building properties in detergent applications.

It was found rather surprisingly that the tertiary amides of formula I and formula II have particular properties compared to other amine based surfactants and more specifically, compared to the structurally related secondary aminoamides (e.g. DMAPA amides).

For instance when bisDMAPA is reacted with a C8 fatty methyl ester (or a C8 fatty acid) it was surprisingly found that the resulting compound is completely miscible with both water and dodecane at temperatures up to 40° C. This amphiphilic nature shows that these molecules can be used as efficient solubilizers, but also with respect to their use in agricultural compositions, explains their broad compatibility with hydrophilic and lipophilic active ingredients. Furthermore, they can be used efficiently in highly concentrated (so-called 'high load') agrochemical compositions to prevent phase separation to occur. The amphiphilic behaviour of the bisDMAPA amides is further illustrated in example 4.

In view of the amphiphilic nature of the tertiary amide, the agrochemical composition of the present invention preferably comprises at least two active ingredients including at least one hydrophilic active ingredient and at least one lipophilic active ingredient.

The hydrophilicity or lipophilicity of the active ingredient can be defined by its $K_{ow}$ value, i.e. by its octanol-water partition coefficient. This coefficient is defined as the ratio (at equilibrium) of the active ingredients concentration in the octanol phase to its concentration in the aqueous phase of a two-phase octanol/water system. The higher the $K_{ow}$ value, the more non-polar (hydrophilic) the compound. The parameter is measured using low solute concentrations and this at room temperature (20° C.). In the present specification a hydrophilic active ingredient is defined as a compound having a log $K_{ow}$ value lower than 0 whilst a lipophilic active ingredient is defined as a compound having a log $K_{ow}$ value higher than or equal to 0 (measured at a temperature of 20° C.). Since for charged compounds the $K_{ow}$ value is dependent from the pH, it is measured for such compounds at the pH of the agrochemical composition. Hereunder are some examples of known log $K_{ow}$ values of active ingredients:

| Glyphosate | −3.2 | (at pH 7) |
|---|---|---|
| Carfentrazone-ethyl | 3.4 | |
| Fenoxaprop-P-ethyl | 4.3 | |
| Dicamba | −1.9 | (at pH 7) |
| Atrazine | 2.6 | |
| 2,4-D | −0.8 | (at pH 7) |
| Nicosulfuron | 0 | (at pH 7) |
| Bentazone | −0.5 | (at pH 7) |

Another example of the particular properties of the bis-DMAPA amides was observed, when the reaction product of bisDMAPA and a fatty acid was quaternized with methyl chloride to form a diquat surfactant. These diquat surfactants were found to still have good solubilities at low temperatures as illustrated in Example 5.

It was surprisingly found that this diquat surfactant was less toxic and irritating than a monoquat surfactant (prepared from the corresponding primary amine) and it was also surprisingly found that this diquat showed good compatibility with anionic surfactants and even showed foam boosting properties (examples 6, 7).

The present invention also relates to the use of the tertiary amide of formula (I) or (II) as an adjuvant in an agrochemical composition. This agrochemical composition preferably comprises a pesticide, a plant growth regulator and/or a fertiliser. The pesticide is in particular a herbicide, a fungicide, an insecticide and/or an acaricide. The pesticide is preferably a systemic pesticide and the fertiliser is in particular a foliar fertilizer, i.e. a fertilizer which is applied onto the leaves of the plant and taken up by these leaves. The present invention moreover relates to the agrochemical compositions themselves.

The tertiary amide of formula (I) or (II) can be added as effective adjuvants to both liquid, such as aqueous or solvent based SL, EC or SC formulations, and to solid agricultural compositions (which are in particular in a powdery or granular form) containing pesticides, such as herbicides, acaricides, fungicides and insecticides, plant growth regulators and/or fertilisers. The liquid composition could be in the form of a solution, an emulsion (including microemulsions) or a suspension. The herbicide may be selected from the following chemical families (the site of action being indicated between brackets): glycines (inhibition of EPSP synthesis), phenoxy carboxylic acids (synthetic auxine), benzoic acids (synthetic auxine), thiazolinones (inhibition of protoporphyrinogen oxidase), phosphinic acids (inhibition of glutamine synthetase), diphenyl ethers (inhibition of protoporphyrinogen oxidase), imidazolines (inhibition of acetolactate synthetase), sulphonyl ureas (inhibition of acetolactate synthetase), aryloxy phenoxy propionates (inhibition of acetyl coenzyme A carboxylase) and triazines (inhibition of photosynthesis at photosystem II).

Typical examples of herbicides are different amine salts of glyphosate, such as the isopropylamine salt, the dimethylamine salt and the ethylenediamine salts; other salts of glyphosate, such as the potassium, the sesquisodium and the trimethylsulphonium salt; carfentrazone ethyl, glufosinate, salts and esters of 2,4-dichlorophenoxyacetic acid, salts and esters of 4-chloro-2-methylphenoxyacetic acid, bialaphos (=glufosinate ammonium), dicamba, atrazine, diphenylethers (such as bifenox, lactofen and fomesafen), imidazolinones (such as imazapic, imazapyr and imazethapyr) and sulphonyl ureas (such as nicosulfuron, prosulfuron and bensulfuron methyl).

The amino compounds of formula (I) and (II) are excellent adjuvants for the water soluble herbicides, e.g. the widely used herbicide glyphosate (glyphosate=N-(phosphonomethyl)-glycine), and the salts thereof. Suitable examples of fungicides are conazole fungicides (such as epoxiconazole and propiconazole) and strobilurin fungicides (such as azoxystrobin and kresoximmethyl).

Other examples of formulations where the amino compounds may be used as adjuvants are fertilizer solutions, in particular micronutrient solutions containing one or several micronutrients, such as iron, manganese, copper, zinc, boron and molybdenum. The micronutrients may be complexed to e.g. aminocarboxylates, such as EDTA, DTPA, HEDTA, EDDHMA and EDDHA. In addition to micronutrients and chelating agents, the formulations may also contain macronutrients, such as nitrogen, phosphorus, potassium, magnesium and sulphur, and pesticides may also be included. These above-mentioned formulations are particularly suitable for foliar applications.

The formulations according to the invention may also contain other additives, such as other surfactants, hydrotropes and preservatives; additives to further enhance pesticidal activity, such as ammonium sulphate; solvents, corrosion inhibitors, thickeners, sequestering agents, antifreeze agents, anti-foam agents, anti-gelling agents and dyes.

The compositions could also contain viscosity reducing agents such as glycerol, ethylene glycol, propylene glycol and low molecular weight polyethylene or polypropylene glycols.

The compositions could be concentrated as well as diluted, "ready to use", solutions. The concentrations may vary within wide limits, and a pesticide formulation could contain 0.01-99.9% by weight of a pesticide, 0-40% by weight of ammonium sulphate and an amount of 0.01-70% by weight of an amino compound of formula (I) or (II). A suitable herbicide is glyphosate, or a salt thereof, which is preferably present in an amount of 0.02-70% by weight. An adjuvant according to the present invention can also advantageously be used in combination with solid agrochemical substances such as strobilurin.

The dissolution of inorganic and organic compounds is an essential operation in everyday life as well as in chemistry. It can be achieved by molecular solubilization in water or organic solvents. However, for different reasons (toxicity, biodegradability, simultaneous solubilization of both polar and unpolar compounds, etc.) chemists and formulators often prefer solubilization with the help of added surfactants. Surfactants are also referred to as wetting agents and foamers. Surfactants lower the surface tension of the medium in which it is dissolved.

Another approach towards the solution of hydrophobic compounds in water is the use of amphiphilic solvents, which present an attempt to combine the advantages of solvents and surfactants. They are commonly used in the fields of coatings, degreasing and numerous other applications (perfumery, inks, etc.). They exhibit the properties of both, the solvents such as volatility and solubilization of organics, and the surfactants, e.g. surface activity, self aggregation in water and co-micellization with surfactants. They are commonly named hydrotropes. Sometimes hydrotropes are added to detergent compositions to prevent phase separation and hence increase the stability and reduce the viscosity.

In the present specification the term "solubilizer" is used as a synonym for "hydrotrope". A hydrotrope is a compound that solubilises hydrophobic compounds in aqueous solutions. Typically, hydrotropes consist of a hydrophilic part and a hydrophobic part (like surfactants) but the hydrophobic part is generally too small to cause spontaneous self-aggregation. Hydrotropes do not have a critical concentration above which self-aggregation 'suddenly' starts to occur (as found for micelle- and vesicle-forming surfactants, which have a critical micelle concentration or cmc and a critical vesicle concentration or cvc, respectively). Instead, some hydrotropes aggregate in a step-wise self-aggregation process, gradually increasing aggregation size. However, many hydrotropes do not seem to self-aggregate at all, unless a solubilisate has been added. Hydrotropes are in use industrially. Hydrotropes are used in detergent formulations to allow more concentrated formulations of surfactants. Examples of hydrotropes include sodium p-toluenesulfonate and sodium xylene sulfonate.

The most widespread hydrotropes today are the ethers derived from ethylene glycol. They have been studied extensively because they exhibit interesting properties, mainly due to the fact that they are soluble not only in water but also in most organic solvents. However, recent toxicological studies have put forward a possible reprotoxic activity. Therefore, some of them have been banned from pharmaceuticals, medicines, and domestic products. Consequently, there is a need for new harmless amphiphilic-solvents possessing comparable physico-chemical properties.

It was surprisingly found that for instance N,N-bis(3-(dimethylamino)propyl)octanamide displayed good hydrotrope properties. On top of that it was found that this compound is completely soluble in water and in dodecane, and thus displays an amphiphilic character.

Detergents, cleaning products, shampoos and other personal care products usually are based on an anionic surfactant. Examples of these anionic surfactants are for instance sodium laureth sulfate (LES) or linear alkylbenzene sulphonates (LAS). Further ingredients for stability and property enhancing reasons are added, like cationic compounds, mainly surfactants, to increase foam stability and improve the conditioning properties of the product. The cationic surfactants will adsorb on the negatively charged surface of the hair and reduce friction as the hydrophobic tails will protrude to the air. The concentration range of cationic amphiphiles is restricted for such applications due to the formation of insoluble precipitates with anionic surfactants at a certain mixing ratio. To find alternatives that are in performance and toxicity equivalent or even more potent to the classically used cationic compounds are still in the focus of interest.

It was surprisingly found that the amidoamine of formula (II) having two quaternary ammonium groups in the hydrophilic head group, showed improved compatibility with anionic surfactants. This property also is in particular advantageous for agrochemical compositions where several types of surfactants need to be used to obtain the desired performance.

Also it was surprisingly found that the water solubility of these diquat surfactants is better than that of standard quaternary surfactants.

The present invention therefore also relates to a detergent composition which contains a tertiary amide of formula (I) or (II) and additionally at least one anionic surfactant. The detergent composition may be a solid, in particular a granular material or a powder, but usually it is a water-based liquid composition containing water.

In the detergent composition, in particular when it is a water-based liquid composition, the tertiary amide of the invention can first of all be used as a solubilizer. In this case, the tertiary amide is preferably a diamine of formula (I) wherein R1 is an aliphatic group having 5-11 carbon atoms and R2, R3, R4 and R5 are alkyl groups with 1-3 carbon atoms, preferably methyl groups. The tertiary amide of the invention can also be used as a surfactant in the detergent composition, in particular when it is a quaternary ammonium salt (di-quat) of formula (II). In order to increase the compatibility between these two surfactants, R6 is preferably an aliphatic group with 1-3 carbon atoms, more preferably a methyl group.

Although the details of the preparation method are described hereunder with particular reference to the preparation of bisDMAPA amide, it will be clear that this preparation method can also be used for preparing the other bisaminopropylamides of the present invention.

BisDMAPA amide adjuvants can be made starting from bisDMAPA (which may be recycled as a byproduct in the production of DMAPA) and a suitable acylating agent. Carboxylic acid, esters, anhydrides or acyl halides (for example acid chloride) can be used as acylating agent.

When acid chlorides are used, the bisDMAPA amide is obtained together with hydrochloric acid. Typically, the hydrochloric acid is scavenged by addition of a base. This can be an excess of starting amine, or a cheaper tertiary amine which is not susceptible to acylation, exemplified by but not limited to triethylamine, pyridine, etc. . . . . In the case of bisDMAPA amides, also the end product still has basic tertiary amine groups that could serve to capture liberated hydrochloric acid. It is known that acid chlorides are highly reactive towards primary and secondary amines, releasing a lot of reaction heat. Therefore, acylations using acid chlorides are generally, but not necessarily, performed at temperatures well below 100° C. to allow fast removal of reaction heat and diluted in a suitable solvent. A suitable solvent is usually a solvent that dissolves both starting materials and end products. Advantageously, any side products generated during the acylation reaction could precipitate from the reaction medium. Suitable solvents can be, as an example: ethers such as diethyl ether, tetrahydrofurane (THF), etc. . . . Halogenated alkanes such as dichloromethane, chloroform, etc. . . . Acylations of highly nucleophilic amines with acid chlorides can be performed in water with addition of inorganic bases such as NaOH or sodium carbonate (the so-called Schotten-Baumann reaction). People skilled in the art may know that organic catalysts may be used to increase the kinetics of the desired acylation reaction according to a principle that is known in the art as "nucleophilic catalysis". Catalysts such a dimethylamino pyridine (DMAP) or pyridine can be used for this purpose.

Carboxylic acids or esters are generally cheaper reagents than the corresponding acid chlorides. Yet, they are less reactive. Nevertheless, bisDMAPA amides can also be formed starting from carboxylic acids or esters using procedures that are known to people skilled in the art. In the case of carboxylic acids, a salt is easily formed upon addition of the amine. Conversion to the corresponding amide is generally performed by applying heat and by removing the reaction water. Temperatures above 100° C. are generally required. Catalysts may be added to facilitate the condensation reaction, such as (solid) acids. Also boric acid has been described as a suitable amidation catalyst for carboxylic acids. For esters on the other hand, basic catalysts are usually used. They can be selected from typical transesterification catalysts such as sodium methoxide, titanates, etc. . . . Also in the case of esters, the reaction benefits from the removal of the alcohol co-product. Also enzymes (lipases and proteases) can be applied as catalysts, allowing lower temperatures to be used.

BisDMAPA was found to react rather difficultly with carboxylic acids and esters under random conditions. However, optimization of reaction parameters allows to obtain the amides in satisfying yield and purity.

EXAMPLES

Example 1: Preparation of bisDMAPA Amide by Acylation of bisDMAPA with an Acid Chloride To a solution of 10% by weight of bisDMAPA in THF and 2 equivalents of triethylamine was added dropwise a 1:1 solution of octanoyl chloride in THF, while the reaction temperature was maintained at a temperature of 40° C. During the addition, a precipitate was formed. After the addition was completed, the reaction mixture was allowed to react for an additional hour at 40° C. Then the mixture was cooled down and the precipitate was removed by filtration. The filter cake was washed with diethyl ether which was combined with the original filtrate. The mixture was then poured into an equal volume of saturated sodium bicarbonate aqueous solution in a separatory funnel. After shaking vigorously, the aqueous phase was separated from the organic phase and washed with a fresh volume of diethyl ether. Phase separation was effectuated again and the two organic phases were combined and dried over magnesium sulphate for 2 hours. Subsequently, the $MgSO_4$ was removed by filtration and the solvent was removed by evaporation under reduced pressure. The obtained oil was found to be 95% pure bisDMAPA octyl amide (yield: 92%).

Example 2: Preparation of bisDMAPA Amide by Acylation of bisDMAPA with a Carboxylic Acid A 1 to 1 molar mixture of bisDMAPA and octanoic acid was heated to a temperature 200° C. in an atmospheric reactor equipped with a stirred and a distillation head. During the course of the reaction, water was removed by the distillation. After four hours, the conversion of octanoic acid was 72%. Then the pressure was reduced slowly to 20 mbar allowing the unconverted starting materials to distill. After the starting materials were removed and collected for recycling, the pressure was decreased further to 10 mbar and the bisDMAPA amide was collected in the distillation head at 95% purity.

Example 3: Biodegradability

Biodegradability test of N,N-bis(3-(dimethylamino) propyl)-octanamide was tested in a Manometric Respirometry Test according to Commission Regulation 440/2008/EC, Method C.4-D of May 30, 2008: Manometric Respirometry Test (EEC Publication N° L142/496, May 2008).
The percentage of biodegradation was 65% after 28 days. As a consequence the compound was considered Readily Biodegradable.

Example 4: Solubilizing Effect

Figure 1:
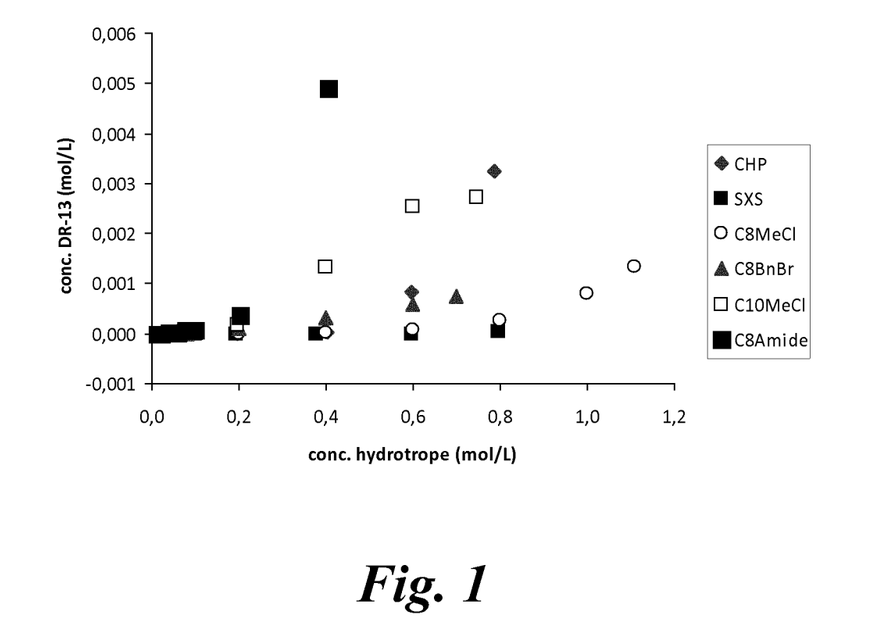
FIG. 1 illustrates the solubilizing effect by condensation products of bis-DMAPA with a $C_8$ fatty methyl ester as described in Example 1.

Due to the unique structure of the tertiary amide compound of formula (I), it can also act as a solubilizer. The solubilising effect by the condensation products of bisDMAPA with a C8 fatty methyl ester has been tested. The result is shown in FIG. 1.

The solubilising properties of the compound was examined by studying spectroscopically the solubilisation of the hydrophobic dye disperse red 13 (DR-13) in water with the help of co-solvents. The solubilization of a hydrophobic compound in water by a co-solvent is known to increase slightly and monotonically at low and moderate co-solvent concentrations and to increase exponentially at very high concentrations. The DR-13 solubilization curve obtained with a surfactant exhibits the classical evolution observed in the case of micellar solubilization; i.e. the DR-13 solubilization increases suddenly when micelles are formed for concentrations above the cmc.

All tested compounds bearing surfactant like properties were highly efficient at low concentrations. An outstanding increase in the amount of solubilized hydrophobic dye was achieved by the addition of small quantities of the non-ionic tertiary amide of formula (I). All substances showed higher efficiencies compared to common hydrotropes like SXS (Sodium Xylene Sultanate) or CHP (cyclohexylpyrrolidone). Obviously the amide met the optimum balance between water solubility and pronounced hydrophobicity, which directly correlates with the hydrotrope efficiency.

Example 5: Solubility of Diquat Surfactant

When the reaction product of bisDMAPA and a fatty acid was quaternized with methyl chloride, a di-quat surfactant was formed. These di-quat surfactants have low solubility temperatures (see Table 1).

TABLE 1

Solubility temperatures of 1 wt % solutions of provided compounds and classical anionic and cationic surfactants

| Substance | Solubility temperatures [° C.] 1 wt % |
|---|---|
| C8BnBr | <0 |
| C8MeCl | <0 |
| C10MeCl | <0 |
| C12MeCl | <0 |
| C14MeCl | <0 |
| C16MeCl | <0 |
| C18MeCl | <0 |
| C8OcBr | <0 |
| C10DeBr | <0 |
| C12DoBr | <0 |
| NaC12 | 25 |
| SDS | 14 |
| CTAB | 25 |
| DTAB | <0 |

C8BnBr = Formula II with R1 = C7H15, R2, R3, R4, R5 = CH3, R6 = Benzyl, Y = Br
C8MeCl = Formula II with R1 = C7H15, R2, R3, R4, R5 = CH3, R6 = CH3, Y = Cl
C10MeCl = Formula II with R1 = C9H19, R2, R3, R4, R5 = CH3, R6 = CH3, Y = Cl
C12MeCl = Formula II with R1 = C11H23, R2, R3, R4, R5 = CH3, R6 = CH3, Y = Cl
C14MeCl = Formula II with R1 = C13H27, R2, R3, R4, R5 = CH3, R6 = CH3, Y = Cl
C16MeCl = Formula II with R1 = C15H31, R2, R3, R4, R5 = CH3, R6 = CH3, Y = Cl
C18MeCl = Formula II with R1 = C17H35, R2, R3, R4, R5 = CH3, R6 = CH3, Y = Cl
C8OcBr = Formula II with R1 = C7H15, R2, R3, R4, R5 = CH3, R6 = C8H17, Y = Cl
C10DeBr = Formula II with R1 = C9H19, R2, R3, R4, R5 = CH3, R6 = C10H21, Y = Cl
C12DoBr = Formula II with R1 = C11H23, R2, R3, R4, R5 = CH3, R6 = C12H25, Y = Cl
NaC12 = Sodium Laurate
SDS = Sodium Dodecyl Sulfate
CTAB = Cetrimonium bromide
DTAB = Dodecyl Trimethyl Ammonium Bromide Example 6: Compatibility with Anionic Surfactants Shampoos and other personal care products usually are based on an anionic surfactant, most commonly sodium laureth sulfate (LES). Further ingredients for stability and property enhancing reasons are added, like cationic compounds, mainly surfactants, to increase foam stability and improve the conditioning properties of the product. The cationic surfactants will adsorb on the negatively charged surface of the hair and reduce friction as the hydrophobic tails will protrude to the air. The concentration range of cationic amphiphiles is restricted for such applications due to the formation of insoluble precipitates with anionic surfactants at a certain mixing ratio. To find alternatives that are in performance and toxicity equivalent or even more potent to the classically used cationic compounds are still in the focus of interest.

To delimit the applicability of the Diquats the compatibility in different ratios with LES was tested in the temperature range between 0° C. and 90° C. The results are summarized in table 2. The methyl quaternized derivatives showed very good compatibility with the anionic surfactant. With a hydrocarbon tail of up to 10 carbon atoms no precipitation was observed and with increasing chain length only a very narrow region of mixing ratios led to an insoluble deposit. In contrast, the octyl and benzyl quaternized derivatives precipitated in a wide range and therefore do not constitute no good alternatives to commonly used cationic compounds in the application necessitating the mixture with anionic surfactants.

Figure 2A:
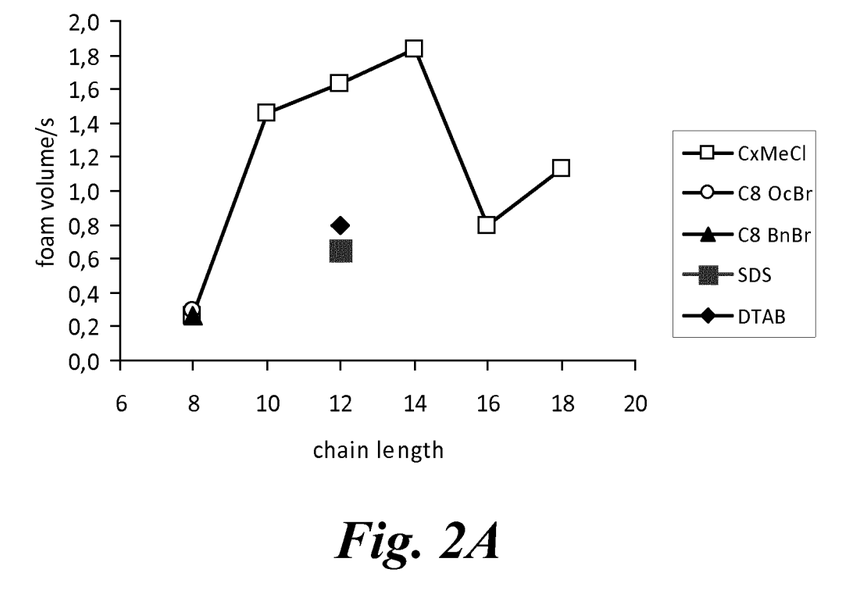
FIGS. 2A and 2B show a comparison of the foam volume per second of pure tertiary amide compounds of formula (II) to classical surfactants (SDS and DTAB) in dependence of the chain length of the R1 fatty chain (FIG. 2A) and in mixture with sodium laureth sulphate (FIG. 2B) and are further described in Example 7.
Figure 2B:
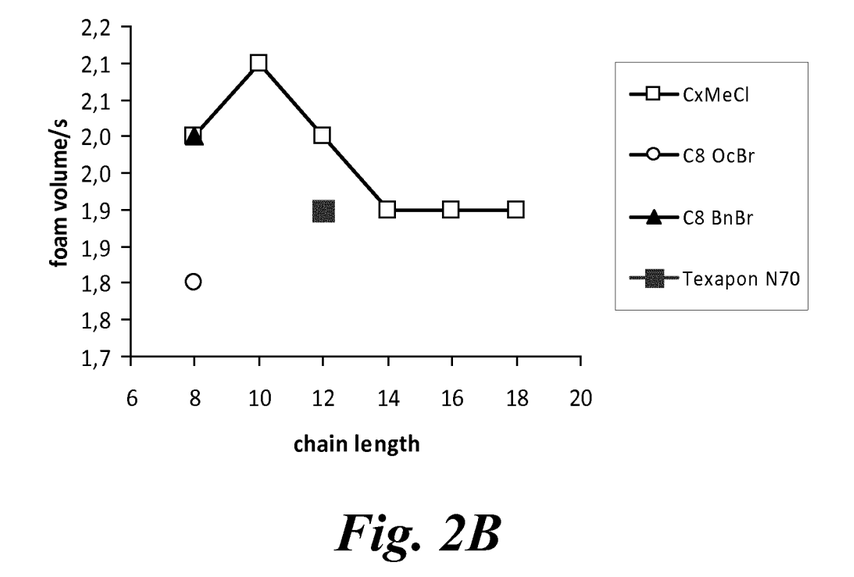

As can be seen in FIG. 2B, the addition of 10% of the tertiary amide compound to a Sodium Laureth sulphate (Texapon N70) solution with 1 wt % surfactant in total led to an increase in foam building. The short chain derivatives showed very efficient foam boosting behaviour.

Example 8: Adjuvant for Glyphosate

The aim of this study was to test different tertiary amide compounds of the present invention on their potency to function as adjuvant for the highly polar and charged herbicide glyphosate. A good adjuvant for glyphosate, seen from the technical point of view, has to fulfill different

TABLE 2

Compatibility observations at ambient temperature of mixtures of Sodium Laureth Sulfate (Texapon N70) with diquats (Formula II type compounds: abbreviations see Table 1) of 1 wt % total surfactant in water

| | % of Diquat | | | | | | | | | |
|---|---|---|---|---|---|---|---|---|---|---|
| | 10% | 20% | 30% | 40% | 50% | 60% | 70% | 80% | 90% | 100% |
| C8MeCl | Cl. | Cl. | Cl. | Cl. | Cl. | Cl. | Cl. | Cl. | Cl. | Cl. |
| C10MeCl | Cl. | Cl. | Cl. | Cl. | Turb. | Cl. | Cl. | Cl. | Cl. | Cl. |
| C12MeCl | Cl. | Cl. | Cl. | Blu. | Cl. | Cl. | Cl. | Cl. | Cl. | Cl. |
| C14MeCl | Cl. | Cl. | Cl. | Prec. | Cl. | Cl. | Cl. | Cl. | Cl. | Cl. |
| C16MeCl | Cl. | Cl. | Visc. | Prec. | Cl. | Cl. | Cl. | Cl. | Cl. | Cl. |
| C18MeCl | Cl. | Cl. | Cl. | Turb. | Visc. | Cl. | Cl. | Cl. | Cl. | Cl. |
| C8OcBr | Cl. | Cl. | Blu. | Blu. | Turb. | Turb. | Turb. | Cl. | Cl. | Cl. |
| C8BnBr | Cl. | Cl. | Cl. | Prec. | Prec. | Prec. | Prec. | Prec. | Prec. | Cl. |

Cl. = Clear
Blu. = Bluish
Visc. = Viscous
Prec. = Precipitate
Turb. = Turbid

Example 7: Foam Boosting Properties

With the diquat surfactants of formula (II) generally foam can be produced with higher efficacy than with classical surfactants like SDS (Sodium Dodecyl Sulfate) and DTAB (Dodecyl trimethyl ammonium bromide). The results of the tests performed in this example are represented in FIGS. 2 A and B.

These figures show a comparison of the foam volume per second of pure tertiary amide compounds of formula (II) to classical surfactants (SDS and DTAB) as a function of the chain length of the R1 fatty chain (FIG. 2A) and in mixture with Sodium Laureth sulphate (FIG. 2B). The foam volume per second reached a maximum at a chain length of C14 and then decreased drastically with increasing number of C atoms in the hydrophobic tail. Generally foaming is more successful the more efficient surface tension is reduced by a surfactant. The effect of surface tension reduction was less pronounced with chainlengths higher than C14, leading to most potent foam builders with chain lengths of C12 and C14. Better foaming than DTAB or SDS potentially was achieved on the one hand due to optimal diffusion rates within the film, as in the case of too fast diffusion rates surfactant molecules in the bulk liquid between the bubble walls may reach the weak spot in the film before surface transport operates. In this case, the weak spot would not be repaired. On the other hand the higher electrostatic repulsion, caused by the double charged headgroups, increases film stability. The thinning of a bubble wall proceeds until charged groups on opposite faces of the wall become sufficiently close to cause electrical repulsion. This repulsion prevents further film thinning.

functions. The adjuvant must provide a good wetting of the leaf surface, must facilitate the foliar penetration of glyphosate under a wide range of climatic conditions and should have low or no phytotoxicity to prevent inhibition of glyphosate translocation in the weeds and to prevent crop damage when used in glyphosate-resistant crops. In a previous study a screening procedure for testing adjuvants for glyphosate was developed (de Ruiter et al 1998). Wheat plants were used as a model for difficult to wet grasses and black nightshade was used as a model for a plant with an easy to wet but difficult to permeate leaf surface.

Plant Material.

Black nightshade and winter wheat (cv. Ilias) were grown in a growth chamber under 14 h of light, at 18/12 (±0.5) ° C. (day/night) temperature, and in 70/80 (±5)% (day/night) relative humidity. Light was provided by high-pressure mercury lamps and fluorescent tubes to give 160 pmol m$^{-2}$ s$^{-1}$ at leaf level. The plants were grown in 11-cm-diam plastic pots filled with a mixture of sand and humic potting soil (1:2 by volume). The pots were placed on subirrigation matting, which was wetted daily with a half-strength nutrient solution. After emergence, the wheat seedlings were thinned to six plants per pot for the efficacy experiments. Black nightshade seedlings were thinned to one plant per pot. Black nightshade and wheat were treated at the four- and the three-leaf stage, respectively. The fresh weights of the plants were measured 14 days after treatment (14 DAT; black nightshade) or 21 days after treatment (21 DAT; wheat).

Herbicide Application.

The glyphosate solutions were applied with an air-pressured laboratory track sprayer having 1.2-mm nozzles fitted with a perforated (0.6 mm) whirling pin and delivering 200 L/ha at 303 kPa.

Treatment Solutions.

A list of the adjuvants tested is presented in Table 3. The adjuvants were added to the unformulated monoisopropylamine salt of glyphosate [MON 8717 (glyphosate IPA salt 648 g ai/L=2.84 M without adjuvant) (ai=active ingredient)] at a concentration of 0.25% (w/v) active adjuvant compound. Demineralized water was used as the carrier. A sub-optimal rate of glyphosate, giving (ideally) a 0-20% growth reduction without adjuvant, was used to demonstrate the adjuvant effects. Based on previous work, these rates were 20.3 g ae/ha (equivalent to 0.6 mM) on black nightshade and 77.8 g ae/ha (equivalent to 2.3 mM at 200 L/ha) on wheat (ae=acid equivalent).

Results.

The results are listed in Table 3. The fresh weight of the untreated plant was taken as a reference (100%). The lower the fresh weight of the treated plant, the more potent the adjuvant. An industrial standard was also included in the test series.

with a perforated (0.6 mm) whirling pin and delivering 200 L/ha at 303 kPa. The following herbicide was used in the treatment solutions: Carfentrazone-ethyl, Spotlight Plus (FMC) ME formulation, 60 g a.i./L.

Treatment Solutions.

The adjuvant was included in the treatment solution at a concentration of 0.25% (w/v) active adjuvant compound. Demineralized water was used as the carrier. A sub-optimal rate of the herbicide, giving (ideally) a 0-20% growth reduction without adjuvant, was used to demonstrate the adjuvant effects.

Experimental Design and Data Analysis.

The experiment was conducted with four replicates per experiment according to a completely randomized design.

Results.

The results (average values) are listed in Table 4. Adding the adjuvant to the herbicide clearly increased the potency of the herbicide.

TABLE 3

Results of the adjuvant for glyphosate tests

| Adjuvant[1] | Fresh Weight SOLNI (g) | Relative weight SOLNI (%) | Fresh Weight WHEAT (g) | Relative weight WHEAT (%) |
|---|---|---|---|---|
| None | 11.6 | 100 | 17.6 | 100.0 |
| only IPA-glyphosate[2] | 6.4 | 55.2 | 12.6 | 71.7 |
| $R_2, R_3, R_4, R_5 =$ —$CH_3$<br>$R1 =$ —$C_7H_{15}$ | 1.6 | 14.1 | 2.3 | 13.0 |
| $R_2, R_3, R_4, R_5, R_6 =$ —$CH_3$<br>$R1 =$ —$C_{11}H_{23}$ | 5.8 | 50.0 | 14.8 | 83.8 |
| $R_2, R_3, R_4, R_5, R_6 =$ —$CH_3$<br>$R1 =$ —$C_{17}H_{35}$ | 2.8 | 24.0 | 14.7 | 83.5 |
| $R_2, R_3, R_4, R_5 =$ —$CH_3$<br>$R_6 =$ —$CH_2CH_2OH$<br>$R_1 =$ —$C_7H_{15}$ | 4.9 | 42.0 | 13.7 | 78.0 |
| Agnique GPU[3] | 1.1 | 9.4 | 1.6 | 8.8 |

[1]Each adjuvant was included at 0.25% w/v (2.5 g/L)
[2]IPA-glyphosate: unformulated isopropylamine salt of glyphosate: for SOLNI: 0.6 mM (equivalent to 20.3 g ae/ha at 200 L/ha) & for WHEAT: 2.3 mM (equivalent to 77.8 g ae/ha at 200 L/ha) (ae = acid equivalent)
[3]Agnique GPU: mixture of tallow amine ethoxylates and glycols

Example 9: Adjuvant for Carfentrazon-ethyl

The aim of this study was to test if the N,N-bis(3-(dimethylamino) propyl)octanamide adjuvant displays potency towards other (more lipophilic) herbicides. In this test we looked at the performance with Carfentrazone-ethyl (Spotlight Plus from FMC) on common lambsquarter (*Chenopodium album* L.; CHEAL).

Plant Material.

Common lambsquarters (*Chenopodium album* L.; CHEAL) were grown in a growth chamber under 14 h of light, at 18/12 (±0.5) ° C. (day/night) temperature, and in 70/80 (±5)% (day/night) relative humidity. Light was provided by high-pressure mercury lamps and fluorescent tubes to give 250 pmol m$^{-2}$ s$^{-1}$ at leaf level. The plants were grown in 11-cm-diam plastic pots filled with a mixture of sand and humic potting soil (1:2 by volume). The pots were placed on subirrigation matting, which was wetted daily with a half-strength nutrient solution. After emergence, the seedlings were thinned to two plants per pot for the efficacy experiments. The common lambsquarters were treated at the four-leaf stage. The fresh weights of the plants were measured 7 days after treatment (7 DAT).

Herbicide Application.

The treatment solutions were applied with an air-pressured laboratory track sprayer having 1.2-mm nozzles fitted

TABLE 4

Results of the adjuvant for Carfentrazon-ethyl test

| Herbicide | Fresh Weight CHEAL (g) No treatment | Fresh weight CHEAL (g) Only herbicide | Fresh Weight CHEAL (g) Herbicide + Adjuvant |
|---|---|---|---|
| Carfentrazon-ethyl | 9.0 | 4.9 | 0.7 |

Example 10: Adjuvant for Dicamba

The aim of this study was to test if the N,N-bis(3-(dimethylamino) propyl)octanamide adjuvant displays potency towards other (more lipophilic) herbicides. In this test the performance with Dicamba OMA-salt (Banvel formulation) on Black nightshade was looked at.

Plant Material.

Black nightshade (*Solanum nigrum* L.; SOLNI) was grown in a growth chamber under 14 h of light, at 18/12 (±0.5) ° C. (day/night) temperature, and in 70/80 (±5)% (day/night) relative humidity. Light was provided by high-pressure mercury lamps and fluorescent tubes to give 250 pmol m$^{-2}$ s$^{-1}$ at leaf level. The plants were grown in 11-cm-diam plastic pots filled with a mixture of sand and humic potting soil (1:2 by volume). The pots were placed on subirrigation matting, which was wetted daily with a half-strength nutrient solution. After emergence, the seedlings were thinned to one plant per pot for the efficacy experiments. Black nightshade was treated at the four-leaf stage. The fresh weights of the plants were measured 16 days after treatment (16 DAT).

Herbicide Application.

The treatment solutions were applied with an air-pressured laboratory track sprayer having 1.2-mm nozzles fitted with a perforated (0.6 mm) whirling pin and delivering 200 L/ha at 303 kPa. The following herbicide was used in the treatment solutions: Dicamba DMA-salt, Banvel formulation, 480 g a.e./L.

Treatment Solutions.

The adjuvant was included in the treatment solution at a concentration of 0.25% (w/v) active adjuvant compound. Demineralized water was used as the carrier. A sub-optimal rate of the herbicide, giving (ideally) a 0-20% growth reduction without adjuvant, was used to demonstrate the adjuvant effects.

Experimental Design and Data Analysis.

The experiment was conducted with four replicates per experiment according to a completely randomized design.

Results.

The results (average values) are listed in Table 5. Adding the adjuvant to the herbicide clearly increased the potency of the herbicide.

TABLE 5

Results of the adjuvant for Dicamba DMA-salt test

| Herbicide | Fresh Weight SOLNI (g) No treatment | Fresh weight SOLNI (g) Only herbicide | Fresh Weight SOLNI (g) Herbicide + Adjuvant |
|---|---|---|---|
| Dicamba | 11.2 | 10.8 | 6.7 |

Example 11: Adjuvant for Fenoxaprop-P-ethyl

The aim of this study was to test if the N,N-bis(3-(dimethylamino) propyl)octanamide adjuvant displays potency towards other (more lipophilic) herbicides. In this test the performance with Fenoxaprop-P-ethyl was looked at.

Plant material. Wild oat (*Avena fatua* L.; AVEFA) was grown in a growth chamber under 14 h of light, at 18/12 (±0.5) ° C. (day/night) temperature, and in 70/80 (±5)% (day/night) relative humidity. Light was provided by high-pressure mercury lamps and fluorescent tubes to give 250 pmol $m^{-2}$ $s^{-1}$ at leaf level. The plants were grown in 11-cm-diam plastic pots filled with a mixture of sand and humic potting soil (1:2 by volume). The pots were placed on subirrigation matting, which was wetted daily with a half-strength nutrient solution. After emergence, the seedlings were thinned to four plants per pot for the efficacy experiments. The plants were treated at the three-leaf stage. The fresh weights of the plants were measured 21 days after treatment (21 DAT).

Herbicide Application.

The treatment solutions were applied with an air-pressured laboratory track sprayer having 1.2-mm nozzles fitted with a perforated (0.6 mm) whirling pin and delivering 200 L/ha at 303 kPa. The following herbicide was included in the treatment solutions: Fenoxaprop-P-ethyl, Puma EW formulation, 69 g a.i./L.

Treatment Solutions.

The adjuvant was included in the treatment solution at a concentration of 0.25% (w/v) active adjuvant compound. Demineralized water was used as the carrier. A sub-optimal rate of the herbicide, giving (ideally) a 0-20% growth reduction without adjuvant, was used to demonstrate the adjuvant effects.

Experimental Design and Data Analysis.

The test was conducted with four replicates per experiment according to a completely randomized design.

Results.

The results (average values) are listed in Table 6. Adding the adjuvant to the herbicide clearly increased the potency of the herbicide.

TABLE 6

Results of the adjuvant for Fenoxaprop-P-ethyl test

| Herbicide | Fresh Weight Wild Oat (g) No treatment | Fresh weight Wild Oat (g) Only herbicide | Fresh Weight Wild Oat (g) Herbicide + Compound |
|---|---|---|---|
| Fenoxaprop-P-ethyl | 18.3 | 16.4 | 1.4 |

Example 12: Compatibility with High Load Formulations

High load formulations of glyphosate-IPA salt were prepared by mixing the ingredients as indicated in table 7. A formulation containing a glyphosate content of about 450 g a.e./l (a.e.=acid equivalent) was obtained in each case.

TABLE 7

Results of the compatibility improving tests

| | A | B | C | D |
|---|---|---|---|---|
| Glyphosate acid | 170 | 170 | 170 | 170 |
| Base | 57 IPA | 57 IPA | 57 KOH | 57 KOH |
| bisDMAPA amide of formula I with $R_1 = C_7H_{15}$, $R_2, R_3, R_4, R_5$ = Me | 15 | | | 16 |
| DMAPA amide of formula III with $R_1 = C_7H_{15}$ $R_2, R_3$ = Me | | 15 | | |
| Ethomeen T/20 | | | 24 | 24 |
| Water | 129 | 129 | 129 | 129 |
| Viscosity at 20° C. (mPa · s) | 225 | Two phase system | Two phase system | One phase |
| Cloud point | >80° C. | Two phase system | Two phase system | >80° C. |

With DMAPA amides and Ethomeen® (tertiary tallow amine ethoxylate) poor mixing was observed and two phase systems were obtained already at room temperature. Amides based on the bisDMAPA structure were much more compatible with water and led to one phase glyphosate formulations with a high cloud point. Even more, when the bisDMAPA amide was used together with Ethomeen®, again a stable one phase formulation was obtained, indicating that because of their amfiphilic properties, bisDMAPA amides can act as a compatibilizer and a solubilizer.

The invention claimed is:

1. An agrochemical composition containing at least one active ingredient selected from the group consisting of herbicides, characterized in that it further contains a tertiary amide of formula (I)

wherein:
R¹ is an aliphatic group having 5-23 carbon atoms; and
R², R³, R⁴, and R⁵ are independently an aliphatic group with 1-5 carbon atoms.

2. An agrochemical composition according to claim 1, wherein R² and R³ are the same as R⁴ and R⁵.

3. An agrochemical composition according to claim 1, wherein R¹ is an aliphatic group having 5-13 carbon atoms.

4. An agrochemical composition according to claim 1, wherein R¹ is an aliphatic group having 7-21 carbon atoms.

5. An agrochemical composition according to claim 1, characterized in that it is free of the corresponding secondary amide of formula (III):

6. An agrochemical composition according to claim 1, characterized in that it is a liquid composition, wherein said composition is a solution, an emulsion or a suspension.

7. An agrochemical composition according to claim 1, characterized in that it is a solid composition which is in a powdery or granular form.

8. An agrochemical composition according to claim 1, characterized in that it additionally contains at least one anionic surfactant.

9. An agrochemical composition according to claim 1, characterized in that it comprises at least two active ingredients including at least one hydrophilic active ingredient and at least one lipophilic active ingredient.

10. An agrochemical composition according to claim 1, characterized in that said active ingredient is a systemic active ingredient.

11. An agrochemical composition according to claim 1, characterized in that it is formulated for foliar applications.

12. An agrochemical composition according to claim 1, characterized in that it comprises an herbicide selected from the group consisting of glycines, phenoxy carboxylic acids, benzoic acids, thiazolinones, phosphinic acids, diphenyl ethers, imidazolines, sulphonyl ureas, aryloxy phenoxy propionates and triazines.

13. An agrochemical composition according to claim 1, wherein the tertiary amide of formula (I) is present in an amount that increases the effectiveness of the active ingredient.

14. An agrochemical composition according to claim 1, characterized in that it comprises up to 50 moles of the corresponding secondary amide of formula (III):

per 100 moles of said tertiary amide.

* * * * *